(12) United States Patent
Pereira et al.

(10) Patent No.: US 9,706,805 B2
(45) Date of Patent: Jul. 18, 2017

(54) ADAPTER FOR PROTECTIVE HEAD GEAR

(71) Applicant: A.C.E. International, Taunton, MA (US)

(72) Inventors: Jason M. Pereira, Taunton, MA (US); James Watkins, East Taunton, MA (US); Ed Martin, Sharon, MA (US)

(73) Assignee: A.C.E. INTERNATIONAL, Taunton, MA (US)

( * ) Notice: Subject to any disclaimer, the term of this patent is extended or adjusted under 35 U.S.C. 154(b) by 479 days.

(21) Appl. No.: 14/090,591

(22) Filed: Nov. 26, 2013

(65) Prior Publication Data

US 2015/0143669 A1    May 28, 2015

(51) Int. Cl.

| | |
|---|---|
| *A42B 1/22* | (2006.01) |
| *A42B 1/24* | (2006.01) |
| *A45F 5/02* | (2006.01) |
| *A42B 3/04* | (2006.01) |
| *A42B 3/22* | (2006.01) |
| *A61F 9/06* | (2006.01) |

(52) U.S. Cl.
CPC .................. *A42B 1/24* (2013.01); *A42B 3/04* (2013.01); *A42B 3/225* (2013.01); *A45F 5/02* (2013.01); *A61F 9/06* (2013.01); *A45F 2005/025* (2013.01); *Y10T 24/1394* (2015.01)

(58) Field of Classification Search
CPC ........... A42B 3/225; A42B 1/24; A42B 3/222; A42B 3/04; A42B 3/145; F16B 2/20; A61F 9/06; A45F 5/02; A45F 2005/025; Y10T 24/1394

USPC ...................................................... 2/424, 425
See application file for complete search history.

(56) References Cited

U.S. PATENT DOCUMENTS

| | | | |
|---|---|---|---|
| 3,214,768 A | 11/1965 | Bohner | |
| 5,575,009 A * | 11/1996 | Ryvin | A41D 13/1153 2/173 |
| 5,829,103 A | 11/1998 | Allen | |
| 5,867,874 A | 2/1999 | Simpson | |
| 6,481,059 B2 | 11/2002 | Morris | |
| 8,032,993 B2 * | 10/2011 | Musal | A42B 3/145 2/418 |
| 2005/0108857 A1 | 5/2005 | Wartian et al. | |

OTHER PUBLICATIONS

Extended European Search Report for European Patent Application 14194740.8-1705 (dated Jul. 16, 2015).

* cited by examiner

*Primary Examiner* — Clinton T Ostrup
*Assistant Examiner* — Abby Spatz
(74) *Attorney, Agent, or Firm* — McClure, Qualey & Rodack, LLP

(57) ABSTRACT

The adapter comprises a clip with a groove, and a rack that engages with the groove. The clip attaches securely to an edge of a fabric, for example, a panel on a baseball cap. The rack includes an angle adjuster, on which a brow guard, welding helmet, or other protective gear can be mounted.

5 Claims, 22 Drawing Sheets

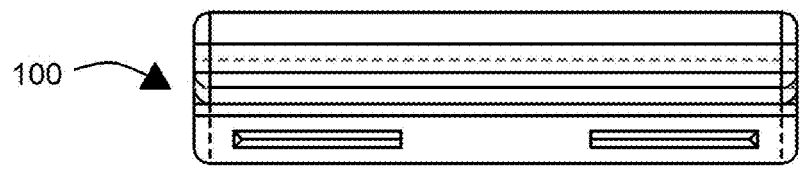
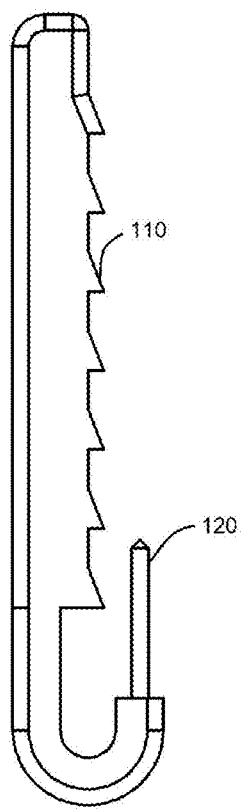
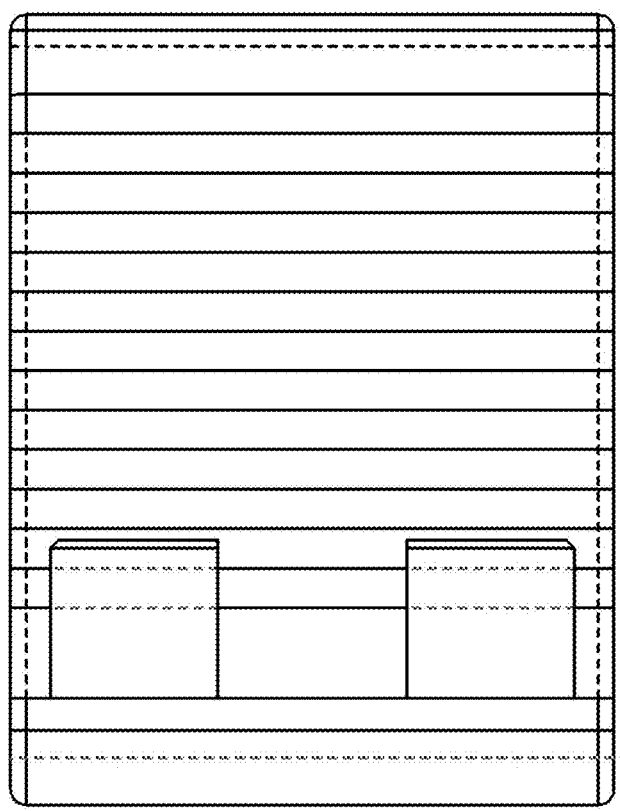
FIG. 1A
FIG. 1B
FIG. 1C

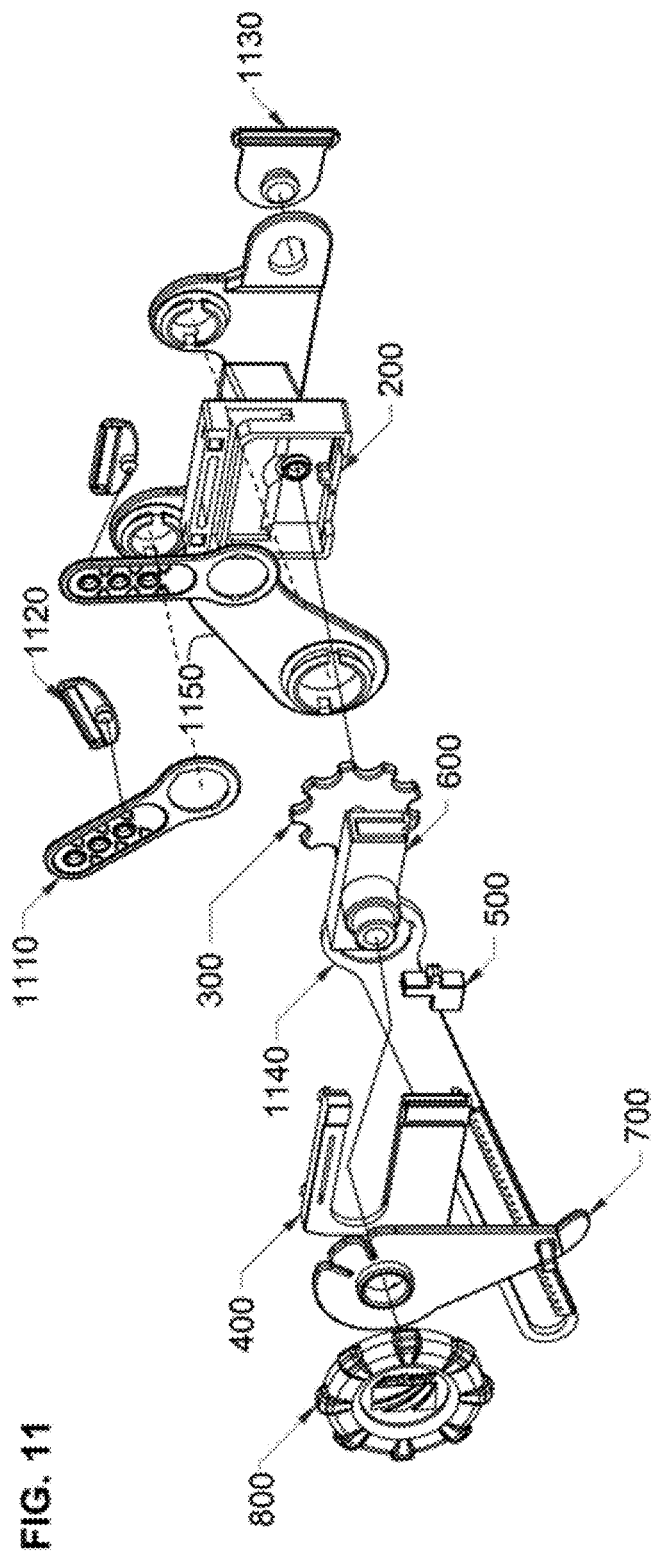

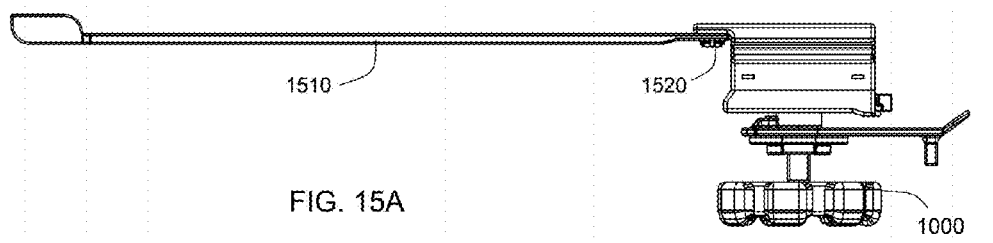
FIG. 15A
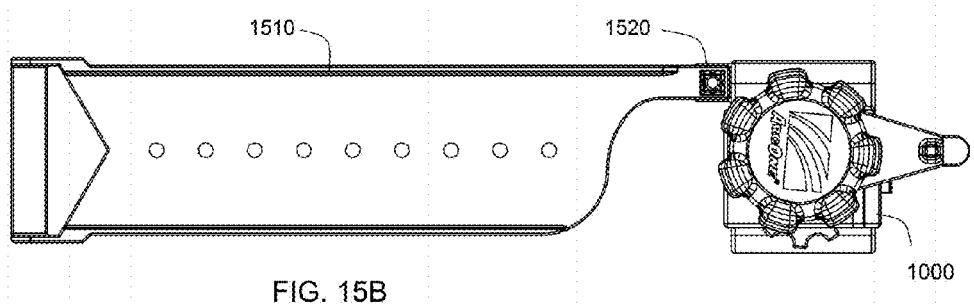
FIG. 15B
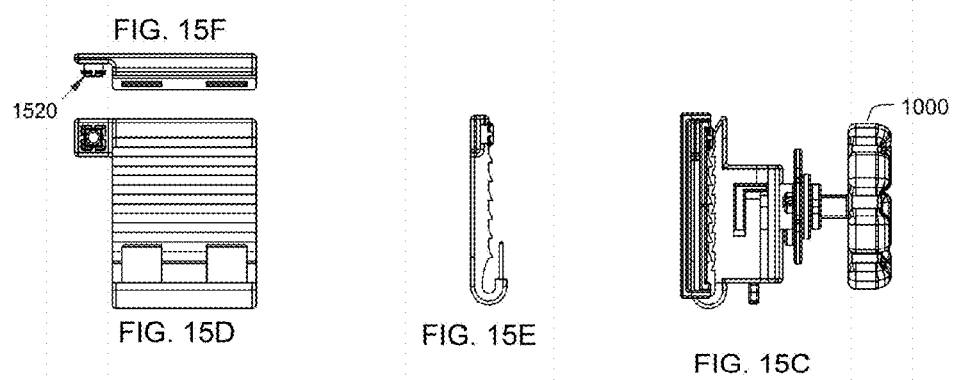
FIG. 15F
FIG. 15D   FIG. 15E   FIG. 15C

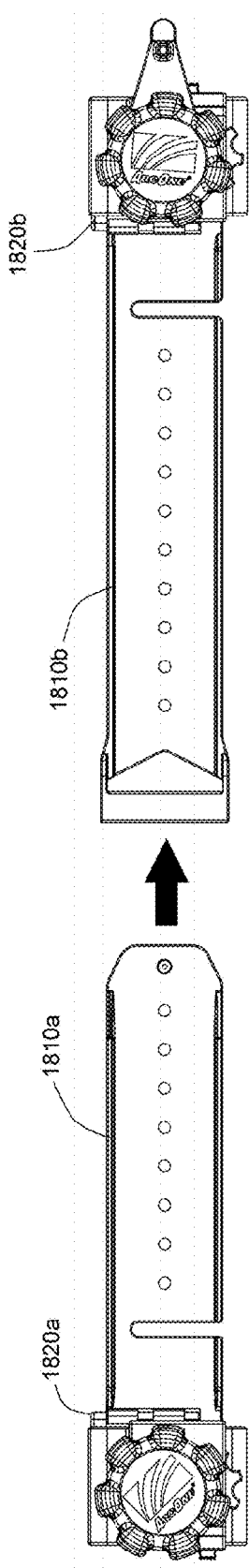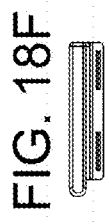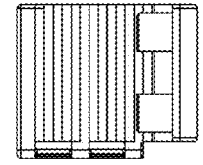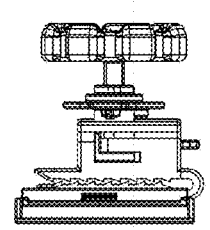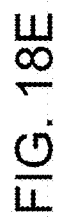

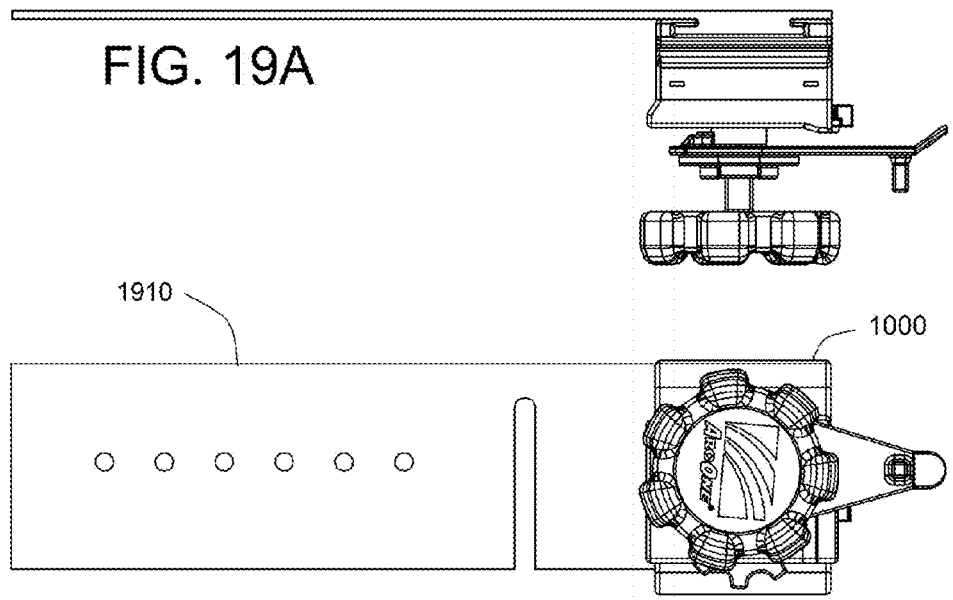
FIG. 19A
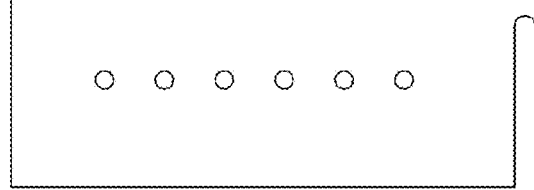
FIG. 19B
FIG. 19C
FIG. 19D  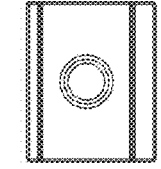 FIG. 19E
FIG. 19F
FIG. 19G  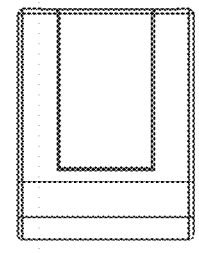
FIG. 19H
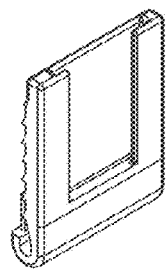
FIG. 19I

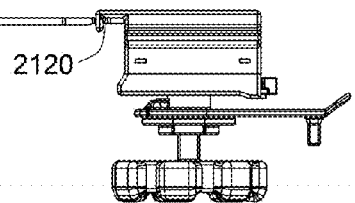
FIG. 21A
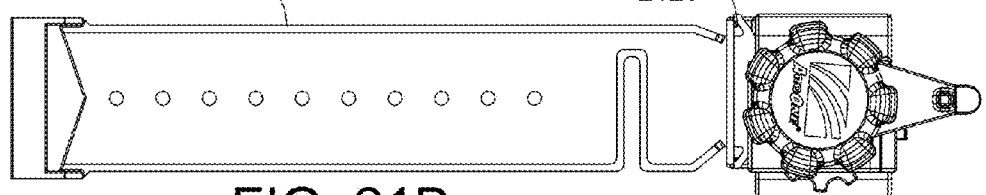
FIG. 21B
FIG. 21E
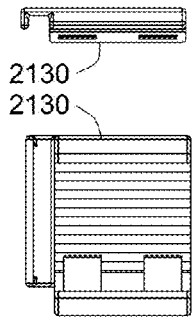
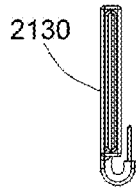
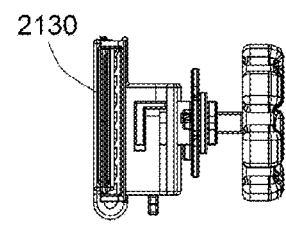
FIG. 21D  FIG. 21F  FIG. 21C

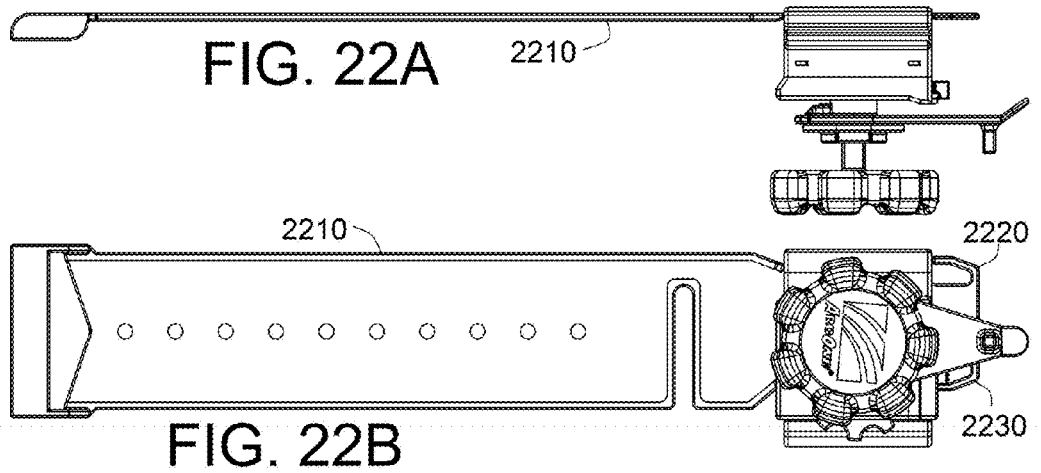
FIG. 22A  
FIG. 22B  
FIG. 22E  
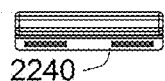
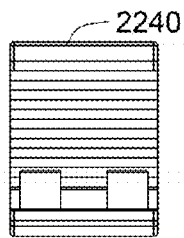
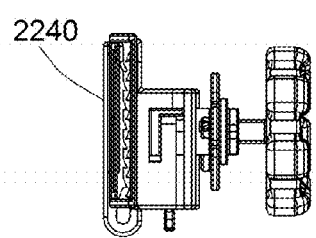
FIG. 22D  FIG. 22F  FIG. 22C

ADAPTER FOR PROTECTIVE HEAD GEAR

BACKGROUND

Field of the Disclosure

The present disclosure relates generally to adapters and, more particularly, to adapters for protective head gear.

Description of Related Art

Certain work environments require protective gear for the head and face (e.g., welding helmet, brow guard, etc.). Sometimes, the protective gear is cumbersome and uncomfortable. Furthermore, the protective gear may not be an optimal fit for all users, thereby further adding to the discomfort. Given the importance of this type of safety equipment, there are ongoing efforts to improve the designs associated with protective gear.

SUMMARY

In some embodiments, an adapter system comprises a clip with a groove, and a rack that engages with the groove. The clip attaches securely to an edge of a panel on, for example, a baseball cap. The rack includes an angle adjuster, on which a brow guard, welding helmet, or other protective gear can be mounted.

Other systems, devices, methods, features, and advantages will be or become apparent to one with skill in the art upon examination of the following drawings and detailed description. It is intended that all such additional systems, methods, features, and advantages be included within this description, be within the scope of the present disclosure, and be protected by the accompanying claims.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIGS. 1A, 1B, and 1C (collectively abbreviated herein as "FIG. 1") are diagrams showing a top view (FIG. 1A), a side view (FIG. 1B), and a front view (FIG. 1C) of one embodiment of an inner panel 100 of a clip.

FIG. 11 is a diagram showing an exploded view of another embodiment of an adapter.

FIGS. 15A, 15B, 15C, 15D, 15E, and 15F (collectively abbreviated herein as "FIG. 15") are diagrams showing one embodiment of a stabilizer.

FIGS. 18A, 18B, 18C, 18D, 18E, and 18F (collectively abbreviated herein as "FIG. 18") are diagrams showing another embodiment of a stabilizer.

FIGS. 19A, 19B, 19C, 19D, 19E, 19F, 19G, 19H, and 19I (collectively abbreviated herein as "FIG. 19") are diagrams showing yet another embodiment of a stabilizer.

FIGS. 21A, 21B, 21C, 21D, 21E, and 21F (collectively abbreviated herein as "FIG. 21") are diagrams showing yet another embodiment of a stabilizer.

FIGS. 22A, 22B, 22C, 22D, 22E, and 22F (collectively abbreviated herein as "FIG. 22") are diagrams showing yet another embodiment of a stabilizer.

DETAILED DESCRIPTION OF THE EMBODIMENTS

Figure 2A:
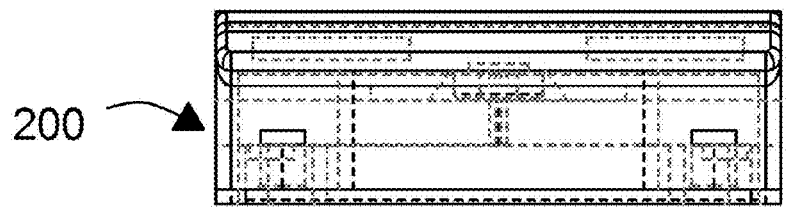
FIGS. 2A, 2B, and 2C (collectively abbreviated herein as "FIG. 2") are diagrams showing a top view (FIG. 2A), a side view (FIG. 2B), and a front view (FIG. 2C) of one embodiment of an outer panel of the clip that engages with the inner panel of FIG. 1.

Various hazardous working environments require the use of protective gear for the head and face (e.g., welding helmet, brow guard, etc.). Depending on the work, the protective gear can sometimes be cumbersome and uncomfortable. Sometimes, the discomfort associated with protective gear becomes a deterrent for the operator to wear the protective gear. In some situations, an uncomfortable fit can also be dangerous, since the discomfort can become a distraction.

The inventive adapter system seeks to provide a more comfortable fit for protective gear. Specifically, the adapter system permits an operator to attach the protective gear to the operator's own cap (e.g., baseball cap, etc.), which will likely provide a better fit and reduce discomfort. For some embodiments, the adapter system comprises a clip with a groove, and a rack that engages with the groove. The clip attaches securely to an edge of a panel on, for example, a baseball cap. The rack includes an angle adjuster, on which a brow guard, welding helmet, or other protective gear can be mounted. As shown in greater detail below, providing a mechanism by which protective gear can be mounted on one's own head covering (e.g., baseball cap) results in a more comfortable fit.

Having provided a general overview of the benefits of the disclosed adapter system, reference is now made in detail to the description of the embodiments as illustrated in the drawings. While several embodiments are described in connection with these drawings, there is no intent to limit the disclosure to the embodiment or embodiments disclosed herein. On the contrary, the intent is to cover all alternatives, modifications, and equivalents. For clarity, embodiments of each of the individual components are first described with reference to FIGS. 1 through 9. Thereafter, one embodiment of an adapter system, which is designed for mounting on a cap (e.g., baseball cap) or other head covering is described with reference to FIG. 10. Another embodiment of an adapter system, which is designed for use with a headmount, is shown in FIGS. 11 and 12. FIGS. 13 through 22 show various embodiments of stabilizers that provide greater stability and security for the adapter system of FIG. 10.

Figure 2B:
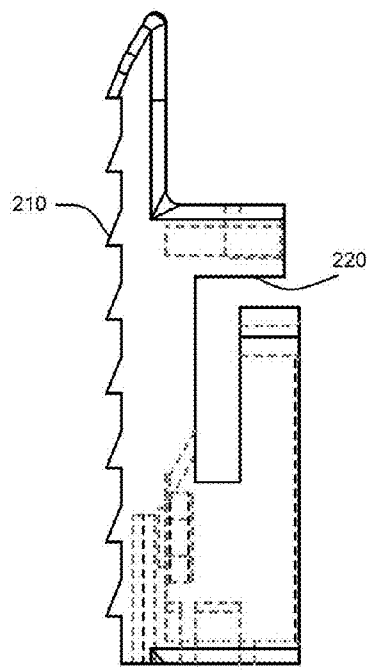
Figure 2C:
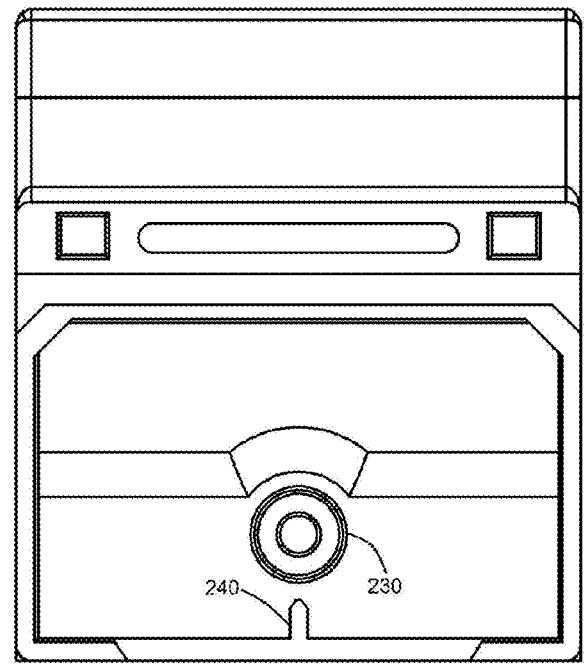

With this in mind, attention is turned to FIGS. 1 and 2, which shown one embodiment of a clip that attaches to a head covering, such as, for example, a baseball cap. Specifically shown are a top view (FIG. 1A), a side view (FIG. 1B), and a front view (FIG. 1O) of one embodiment of an inner panel 100 of the clip, along with a top view (FIG. 2A), a side view (FIG. 2B), and a front view (FIG. 2C) of one embodiment of an outer panel 200 of the clip. As shown in FIGS. 1 and 2, the inner panel (FIG. 1) comprises inner teeth 110, and the outer panel (FIG. 2) comprises outer teeth 210. Together, the inner teeth 110 and the outer teeth 210 form the holding mechanism that secures the clip (FIGS. 1 and 2) to an edge of a baseball cap. It should be understood that the clip can also be secured to other types of head coverings and is not limited to being mounted on a baseball cap. For one embodiment, the inner teeth 110 and the outer teeth 210 have saw-tooth patterns that permit secure clamping around the fabric.

Figure 3A:
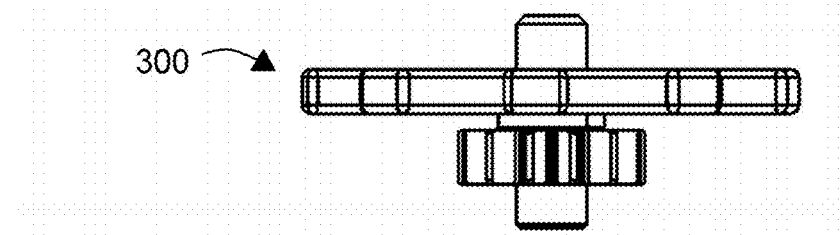
FIGS. 3A, 3B, and 3C (collectively abbreviated herein as "FIG. 3") are diagrams showing a top view (FIG. 3A), a side view (FIG. 3B), and a front view (FIG. 3C), of one embodiment of a pinioned dial that engages with the outer panel of FIG. 2.
Figure 3B:
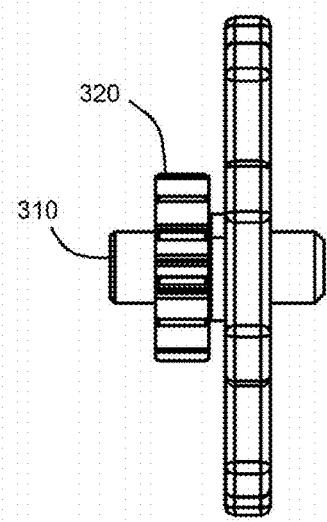
Figure 3C:
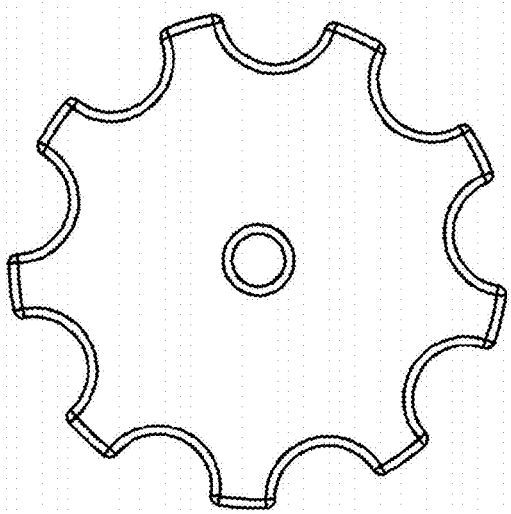

Continuing, FIG. 3 is a diagram showing a top view (FIG. 3A), a side view (FIG. 3B), and a front view (FIG. 3C), of one embodiment of a pinioned dial 300 that engages with the outer panel (FIG. 2). As shown in FIGS. 2 and 3, the outer panel comprises an unthreaded bore 230, and the pinioned dial (FIG. 3) comprises an axle 310 that rotationally mates with the unthreaded bore 230, thereby permitting the pinioned dial (FIG. 3) to rotate with reference to the outer panel (FIG. 2). The pinioned dial (FIG. 3) further comprises a pinion 320, and the outer panel (FIG. 2) also comprises a locking pawl 240 that engages the pinion 320 to inhibit rotation of the pinioned dial (FIG. 3). In other words, in the absence of the locking pawl 240, the pinioned dial (FIG. 3) would be permitted to freely rotate without much resistance. Conversely, the locking pawl 240 provides a finite degree of resistance as it engages the pinion 320, which provides a mechanism for setting the position of the pinioned dial (FIG. 3) to prevent free rotation of the pinioned dial (FIG. 3).

Figure 4A:
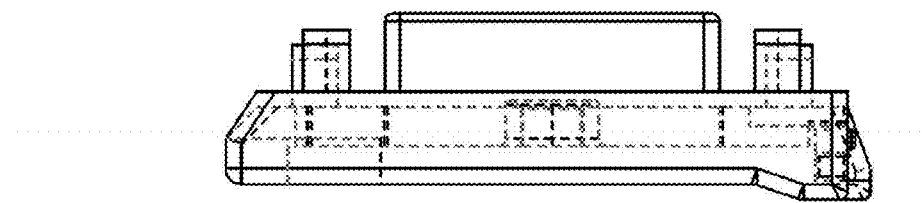
FIGS. 4A, 4B, and 4C (collectively abbreviated herein as "FIG. 4") are diagrams showing a top view (FIG. 4A), a side view (FIG. 4B), and a front view (FIG. 4C) of one embodiment of a cover that engages with the outer panel of FIG. 2.
Figure 4B:
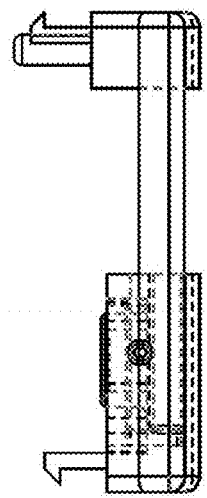
Figure 4C:
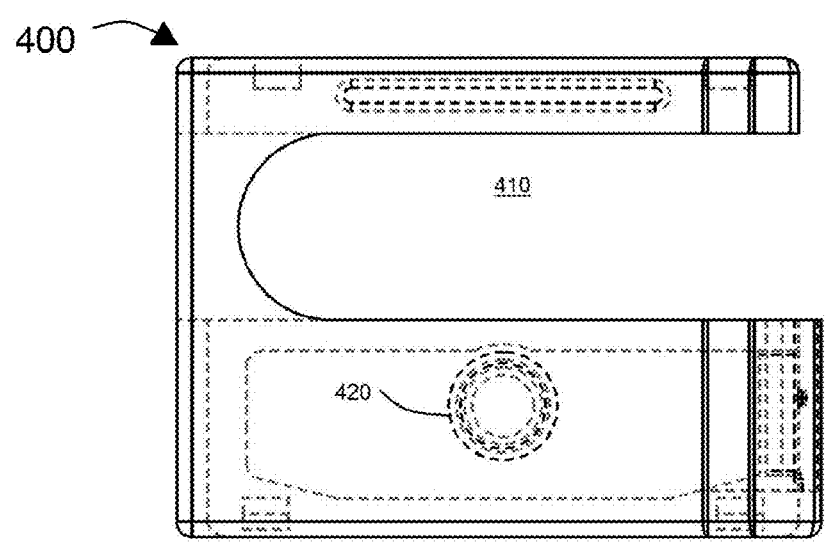

FIG. 4 is a diagram showing a top view (FIG. 4A), a side view (FIG. 4B), and a front view (FIG. 4C) of one embodiment of a cover 400 (FIG. 4), which securely holds the dial (FIG. 3) within the outer panel (FIG. 2). The combination of the cover (FIG. 4), the outer panel (FIG. 2), and the inner panel (FIG. 1) forms the clip. The cover (FIG. 4) comprises a notch 410 that accommodates the axle 310 of the pinioned dial (FIG. 3). Consequently, the pinioned dial (FIG. 3) is able to move translationally with reference to the clip.

Figure 6A:
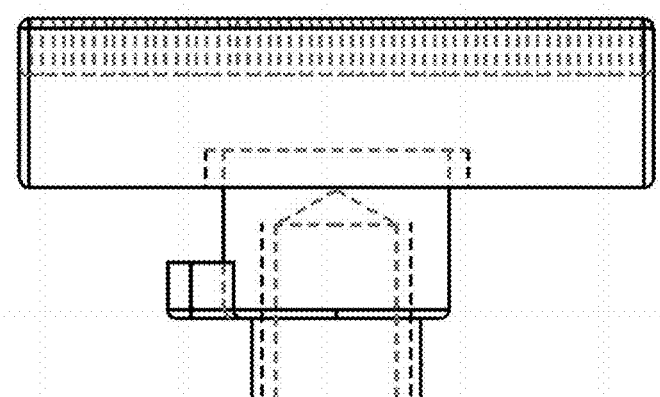
FIGS. 6A, 6B, and 6C (collectively abbreviated herein as "FIG. 6") are diagrams showing a top view (FIG. 6A), a side view (FIG. 6B), and a front view (FIG. 6C) of one embodiment of a rack that forms a rack-and-pinion mechanism with the pinioned dial of FIG. 3.
Figure 6B:
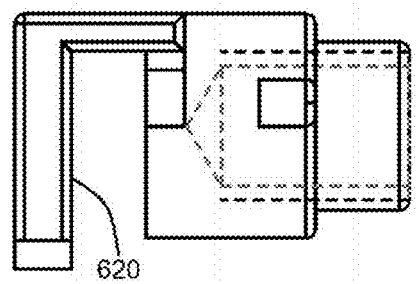
Figure 6C:
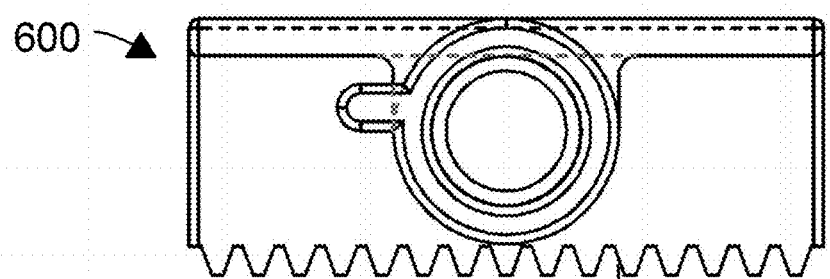

FIG. 6 is a diagram showing a top view (FIG. 6A), a side view (FIG. 6B), and a front view (FIG. 6C) of one embodiment of a rack 600 that forms a rack-and-pinion mechanism with the pinioned dial (FIG. 3). As shown in FIG. 6, the rack comprises rack teeth 610, which engages with the pinion 320 to form a rack-and-pinion mechanism. Thus, when the pinioned dial (FIG. 3) is rotated, this rotational motion of the pinioned dial (FIG. 3) results in a linear movement of the rack (FIG. 6). Consequently, this linear movement permits an operator or user to adjust a distance of a brow-guard, welding helmet, or other protective gear so that it is at an optimal or comfortable distance from the face of the operator or user. The rack (FIG. 6) further comprises a sliding arm 620, and the outer panel (FIG. 2) further comprises a groove 220 that slidably mates with the sliding arm 620. The combination of the groove 220 and the sliding arm 620 permits the rack (FIG. 6) to move linearly with reference to the outer panel (FIG. 2).

Figure 5A:
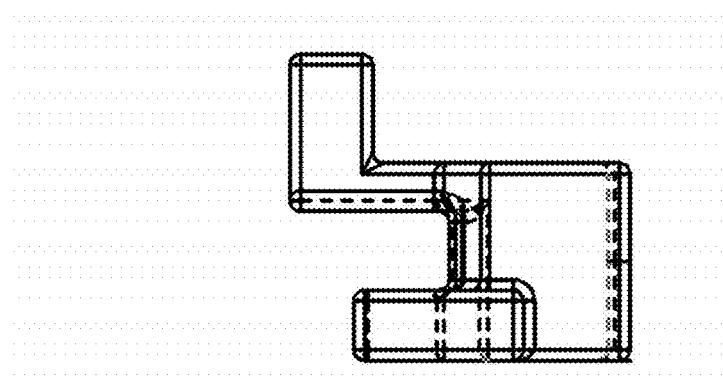
FIGS. 5A, 5B, and 5C (collectively abbreviated herein as "FIG. 5") are diagrams showing a top view (FIG. 5A), a side view (FIG. 5B), and a front view (FIG. 5C) of one embodiment of a slide lock that engages with the cover of FIG. 4.
Figure 5B:
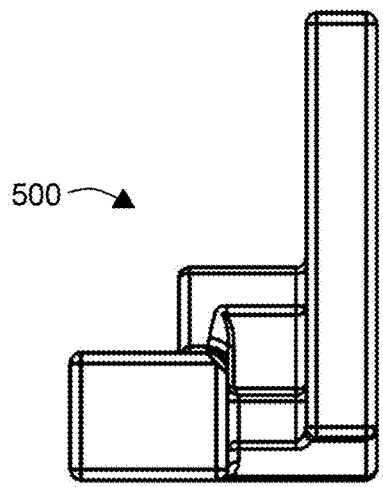
Figure 5C:
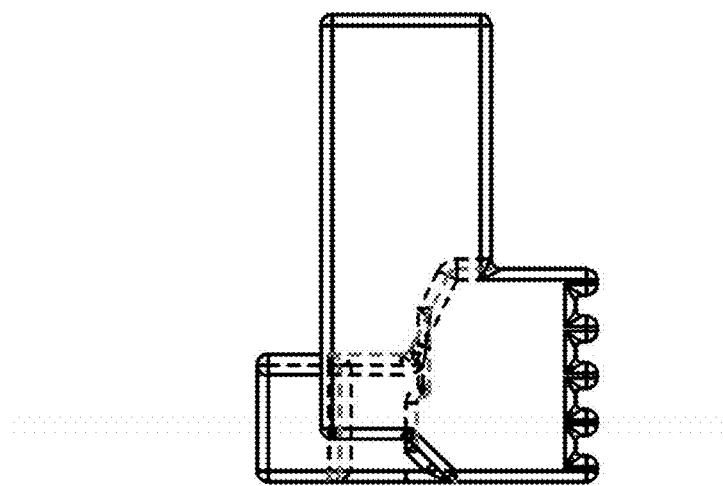

FIG. 5 is a diagram showing a top view (FIG. 5A), a side view (FIG. 5B), and a front view (FIG. 5C) of one embodiment of a slide lock 500 that engages with the cover (FIG. 4). The slide lock (FIG. 5) is positioned at the opening of the notch 410 of the cover (FIG. 4), and can be in either a locked position (where it extends into the notch 410) or an unlocked position (where it does not extend into the notch 410). Consequently, when the rack (FIG. 6) is inside of the notch 410, and the slide lock (FIG. 5) is in the locked position, the slide lock (FIG. 5) prevents the rack (FIG. 6) from disengaging from the groove 220 of the clip. Conversely, when the slide lock (FIG. 5) is in the unlocked position, then the slide lock (FIG. 5) permits the rack (FIG. 6) to disengage from the groove 220 of the clip. As one can appreciate, when in the unlocked position, the rack (FIG. 6) can be quickly released from the groove 220 of the clip by simply pulling the rack (FIG. 6) through the notch 410.

Figure 7A:
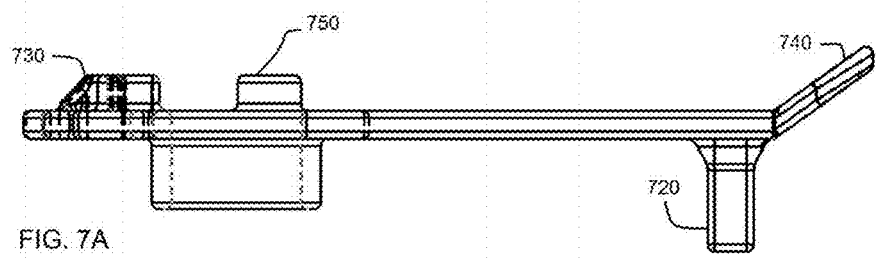
FIGS. 7A, 7B, and 7C (collectively abbreviated herein as "FIG. 7") are diagrams showing a top view (FIG. 7A), a side view (FIG. 7B), and a front view (FIG. 7C) of one embodiment of an angle adjuster that mounts to the rack of FIG. 6 and holds protective gear.
Figure 7B:
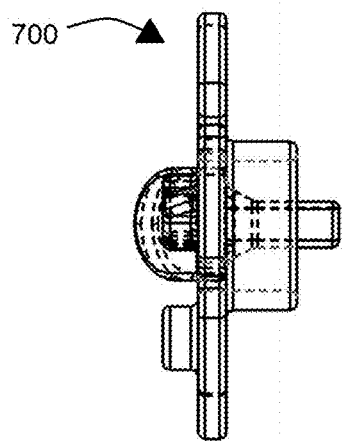
Figure 7C:
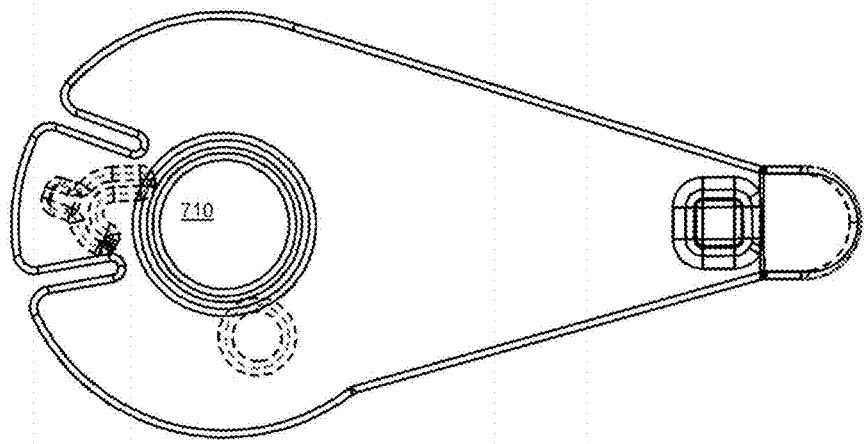
Figure 8A:
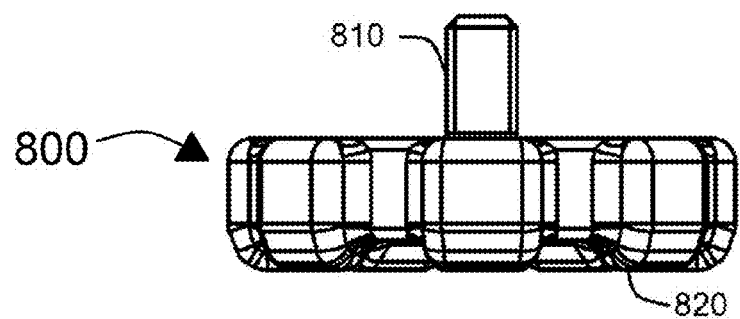
FIGS. 8A, 8B, and 8C (collectively abbreviated herein as "FIG. 8") are diagrams showing a top view (FIG. 8A), a side view (FIG. 8B), and a front view (FIG. 8C) of one embodiment of a knob that engages with the rack of FIG. 6.
Figure 8B:
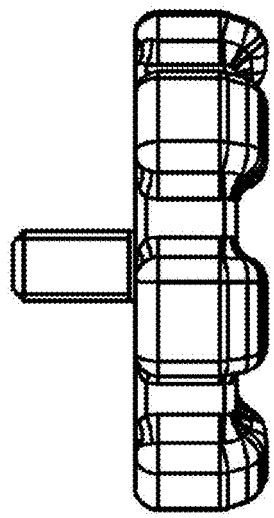
Figure 8C:
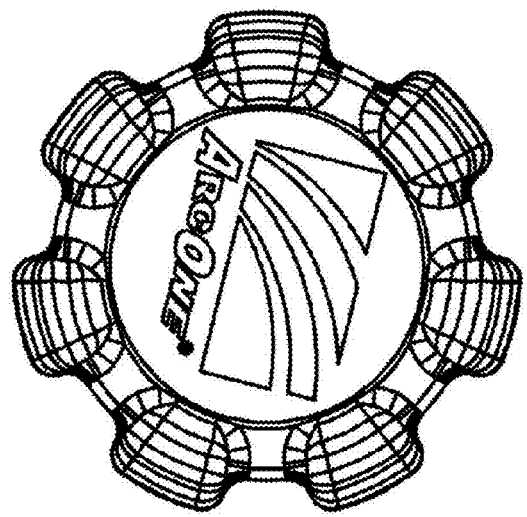

FIG. 7 is a diagram showing a top view (FIG. 7A), a side view (FIG. 7B), and a front view (FIG. 7C) of one embodiment of an angle adjuster 700 that mounts to the rack (FIG. 6) and holds protective gear. FIG. 8 is a diagram showing a top view (FIG. 8A), a side view (FIG. 8B), and a front view (FIG. 8C) of one embodiment of a knob that engages with the rack (FIG. 6). The knob (FIG. 8) comprises a threaded male member 810, and the rack (FIG. 6) comprises a threaded female receptacle 630 that secures to the male member 810. The angle adjuster (FIG. 7) comprises a hole 710 through which the male member 810 inserts. Thus, when assembled, the angle adjuster (FIG. 7) is secured between the knob 800 (FIG. 8) and the rack (FIG. 6), and can be pivoted with reference to the rack (FIG. 6). As a result, when protective gear (e.g., brow guard, welding helmet, etc.) is mounted to the angle adjuster (FIG. 7), the position of the protective gear can be controlled by moving the rack (FIG. 6) forward and backward using the pinioned dial (FIG. 3). Furthermore, the protective gear can be lifted and re-positioned at different angles as a result of being mounted on the angle adjuster (FIG. 7).

Figure 9A:
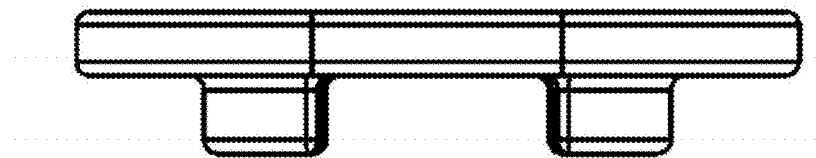
FIGS. 9A, 9B, and 9C (collectively abbreviated herein as "FIG. 9") are diagrams showing a top view (FIG. 9A), a side view (FIG. 9B), and a front view (FIG. 9C) of one embodiment of a bearing that is interposed between the knob of FIG. 8 and the angle adjuster of FIG. 7.
Figure 9B:
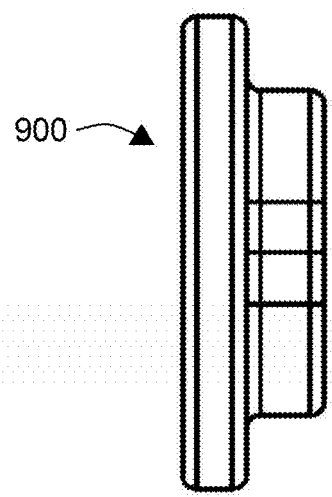
Figure 9C:
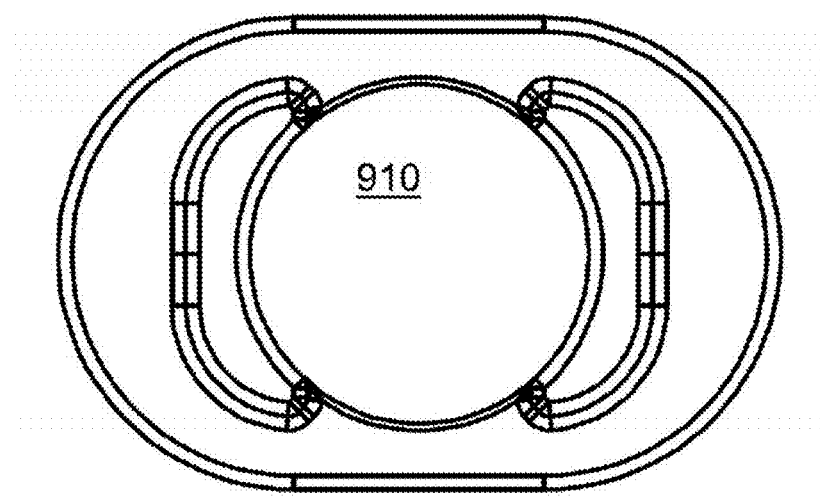

For some embodiments, a bearing can be interposed between the rack (FIG. 6) and the knob (FIG. 8) in place of the angle adjuster (FIG. 7). One embodiment of the bearing 900 is shown with reference to FIG. 9, including a top view (FIG. 9A), a side view (FIG. 9B), and a front view (FIG. 9C).

Figure 10:
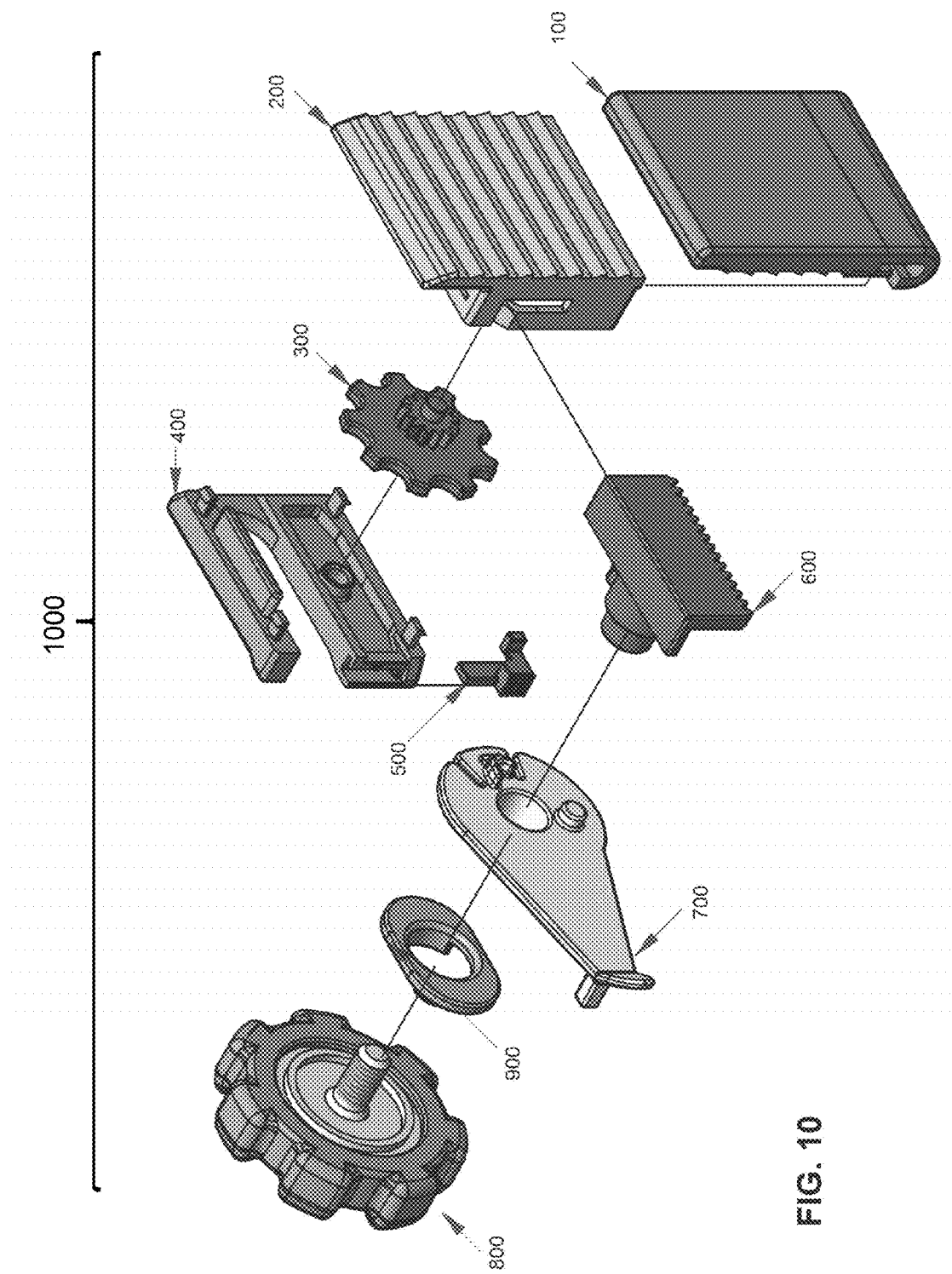
FIG. 10 is a diagram showing an exploded view of one embodiment of an adapter, with all of the corresponding components of FIGS. 1 through 9.

FIG. 10 is a diagram showing an exploded view of one embodiment of an adapter 1000, with all of the corresponding components 100, 200, 300, 400, 500, 600, 700, 800, 900 of FIGS. 1 through 9. As shown in FIG. 10, when fully assembled, the adapter permits an operator or user to adjust the distance between protective head gear and the face of the user or operator by turning the pinioned dial (FIG. 3). Furthermore, the adapter (FIG. 10) permits the operator or user to install protective head gear onto a better fitting head-covering, such as, for example, a baseball cap. Since the angle adjuster (FIG. 7) is pivotally mounted to the rack (FIG. 6), the protective gear (e.g., brow guard, welding helmet, etc.) can be lifted and re-positioned as the user or operator sees fit.

As one can readily appreciate, the adapter (FIG. 10) allows the user or operator to use a more comfortable and better fitting head covering (e.g., one's own baseball cap) in conjunction with protective head gear. As such, the adapter (FIG. 10) produces a better fit and reduces discomfort, thereby improving workplace safety.

Figure 12A:
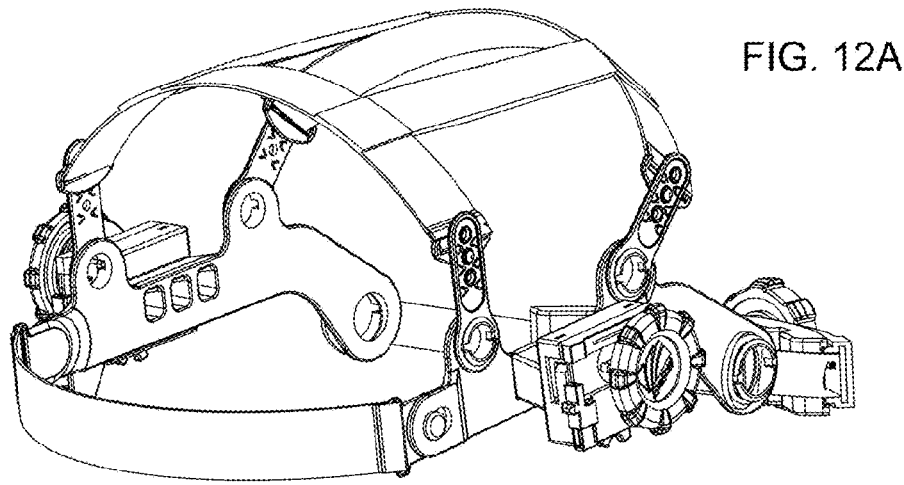
FIGS. 12A, 12B, and 12C (collectively abbreviated herein as "FIG. 12") are diagrams showing an assembled perspective view (FIG. 12A), side view (FIG. 12B), and a top view (FIG. 12C) of the adapter of FIG. 11.
Figure 12B:
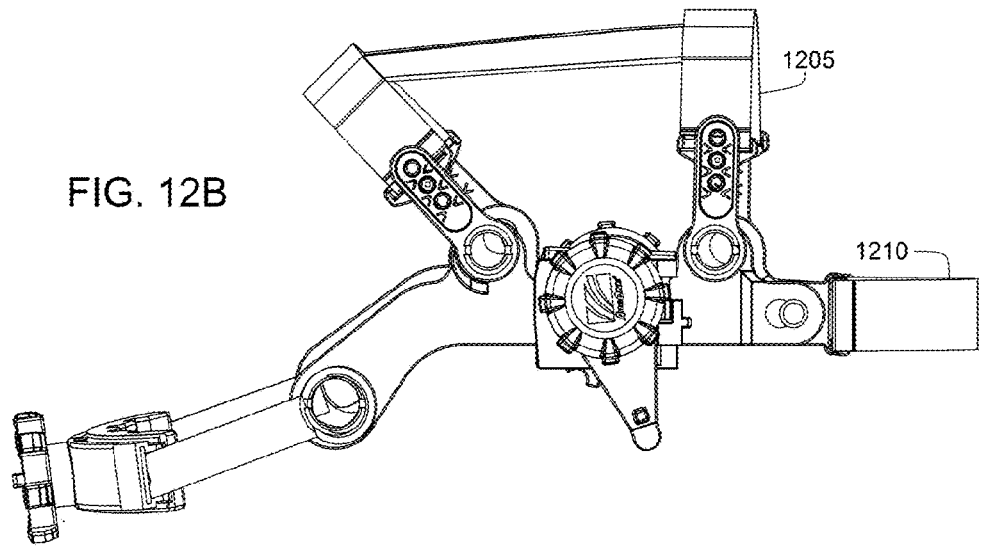
Figure 12C:
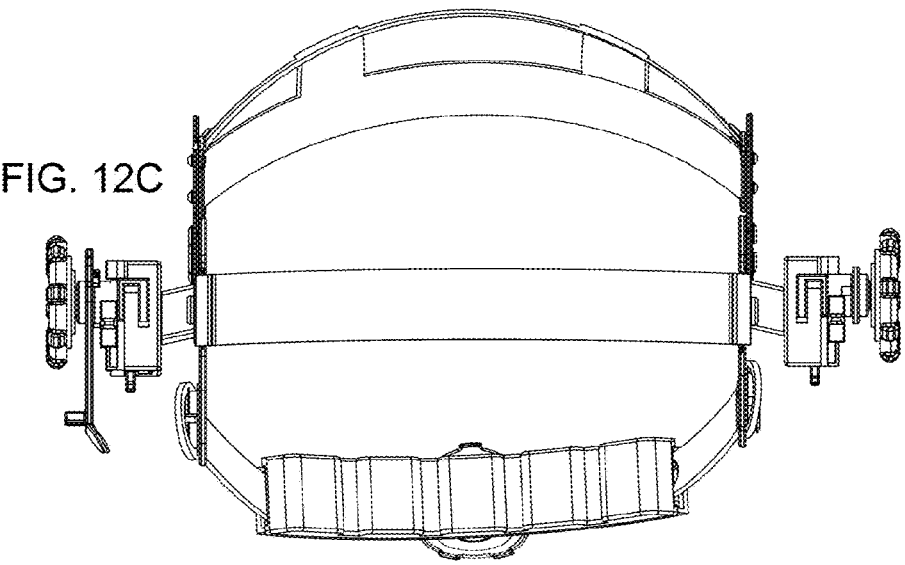

With this in mind, attention is turned to FIGS. 11 and 12, which show another embodiment of an adapter system. Specifically, FIG. 11 shows an exploded view of one embodiment of an adapter system, while FIG. 12 shows an assembled perspective view (FIG. 12A), side view (FIG. 12B), and a top view (FIG. 12C) of the adapter system of FIG. 11. Similar to FIG. 10, this embodiment of the adapter system (FIG. 11) comprises an outer panel (FIG. 2), a pinioned dial (FIG. 3), a cover (FIG. 4), a slide lock (FIG. 5), a rack (FIG. 6), an angle adjuster (FIG. 7), and a knob (FIG. 8). Since these particular components (FIGS. 2 through 8) have already been described above, further discussion of these components is omitted here. However, unlike the adapter of FIG. 10, the adapter of FIG. 11 does not have an inner panel (FIG. 1). Instead, the outer panel (FIG. 2) is mounted to a mount 1150 that forms a part of a head-gear assembly.

The head-gear assembly comprises the mount 1150, a rear strap 1140 that secures to the mount 1150, a top fabric attachment 1120 to attach a top fabric strap 1205, a front fabric attachment 1130 to attach a front fabric strap 1210, and a height adjuster 1110 to adjust fit for better comfort and safety. The rear strap 1140 secures around the head of a user or operator, as shown in FIG. 12, thereby holding the adapter (FIG. 11) in place. As shown in FIG. 12, the rear strap is adjustable to provide a better fit for the operator or user. Additionally, for some embodiments, the front fabric strap and the top fabric strap (as shown in FIG. 12) are adjustable or elastic (or both), thereby improving fit and comfort.

Mounting the adapter system (FIG. 11) to a head-gear assembly provides a stand-alone unit, which permits the user or operator to adjust the distance between the face of the operator or user and the protective head gear (e.g., brow guard, welding mask, etc.). One advantage of the stand-alone unit of FIG. 12 is that it provides greater stability and security than adapter systems (FIG. 10) that are attached to a baseball cap. With this in mind, the adapter system (FIG. 10) can be more-securely attached to a baseball cap by providing stabilizers. Various embodiments to stabilize the adapter system (FIG. 10) are shown with reference to FIGS. 13 through 22.

Figure 13A:
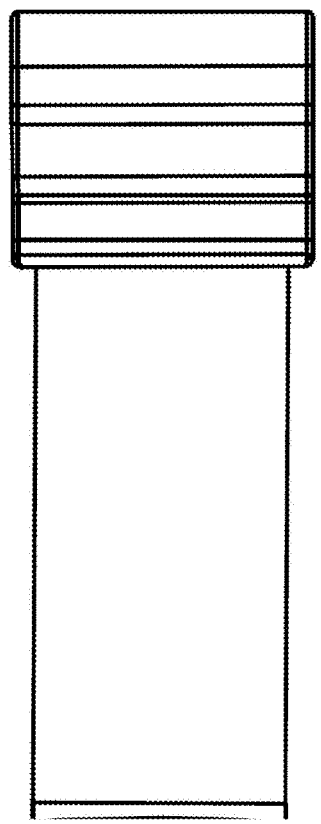
FIGS. 13A and 13B (collectively abbreviated herein as "FIG. 13") are diagrams showing a top view (FIG. 13A) and a side view (FIG. 13B) of one embodiment of a brim clip.
Figure 13B:
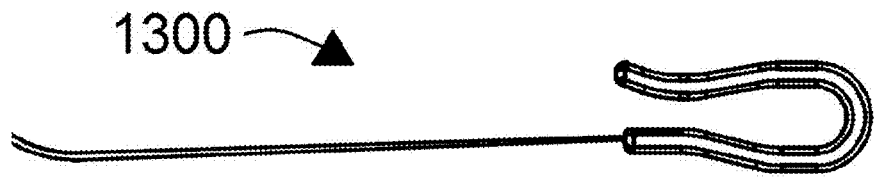
Figure 14A:
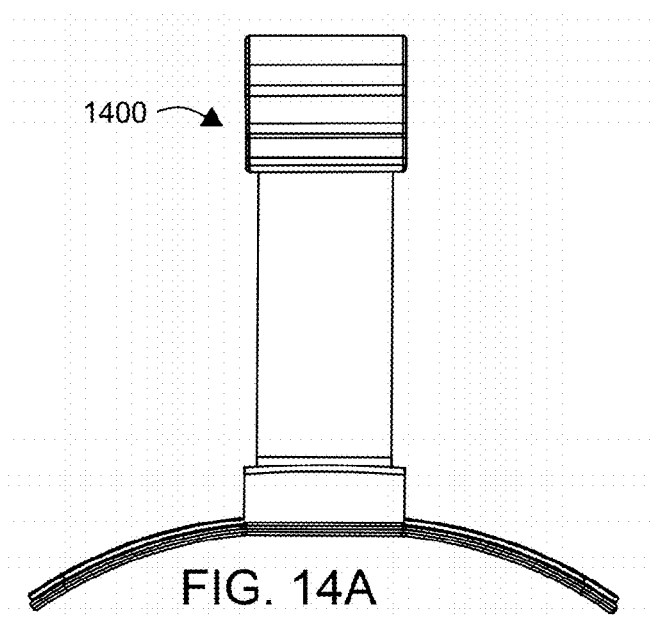
FIGS. 14A, 14B, and 14C (collectively abbreviated herein as "FIG. 14") are diagrams showing a top view (FIG. 14A), a side view (FIG. 14B), and a front view (FIG. 14C) of one embodiment of a gel pad with the brim clip (FIG. 13).
Figure 14B:
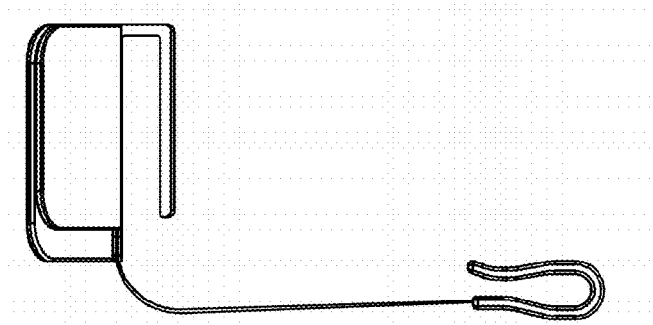
Figure 14C:
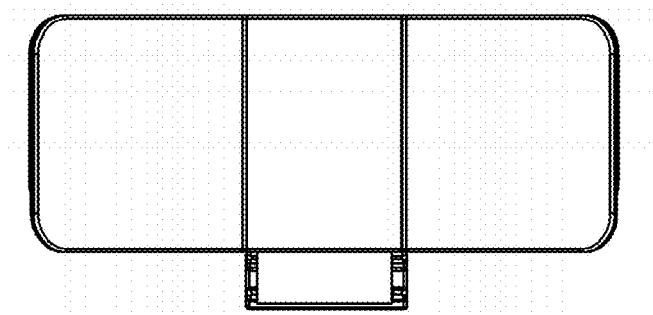
Figure 16A:
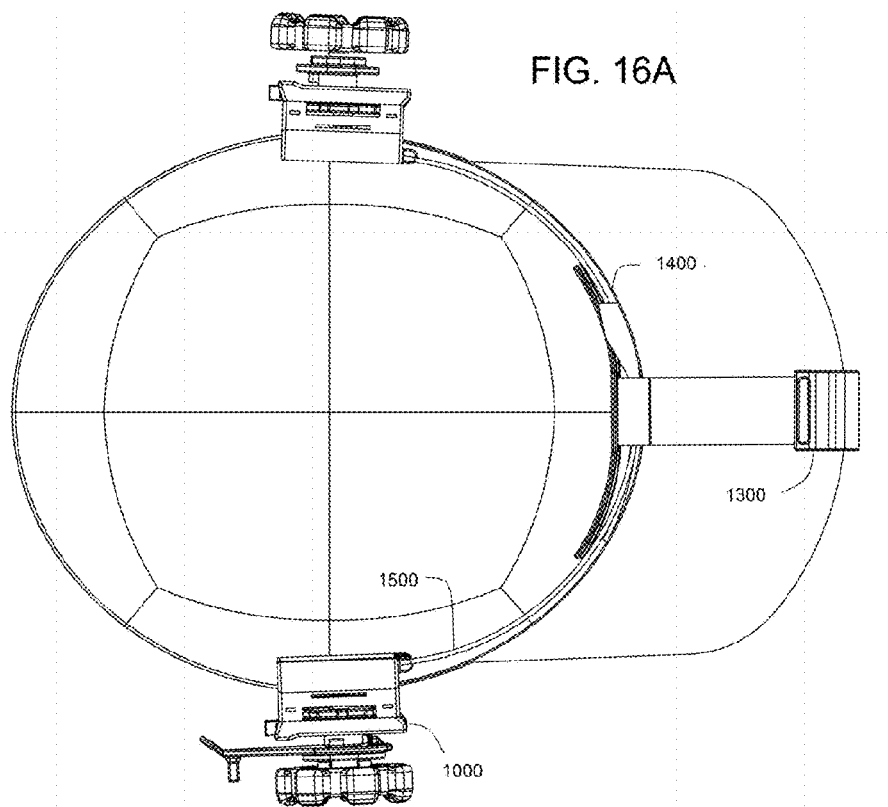
FIGS. 16A, 16B, and 16C (collectively abbreviated herein as "FIG. 16") is a diagram showing a top view (FIG. 16A), a side view (FIG. 16B), and a front view (FIG. 16C) of one embodiment of a baseball cap comprising the adapter (FIG. 10), the brim clip (FIG. 13), the brim gel pad (FIG. 14), and the stabilizer (FIG. 15).
Figure 16B:
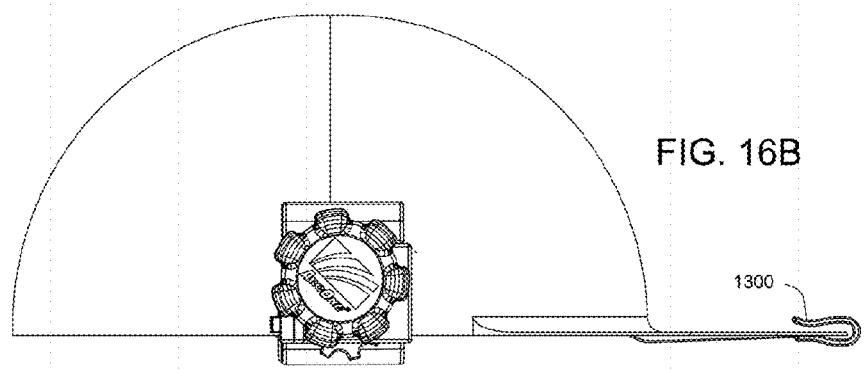
Figure 16C:
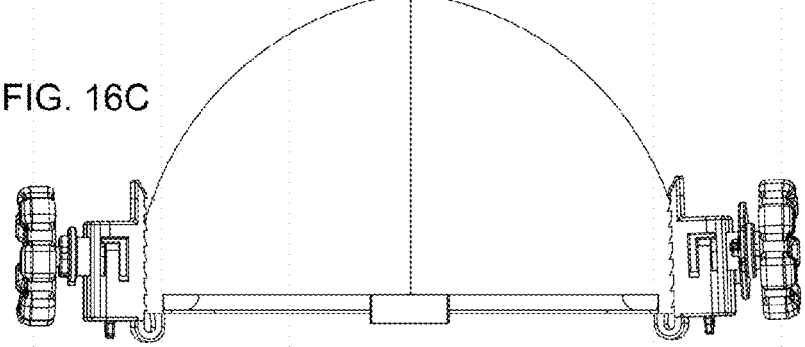
Figure 17:
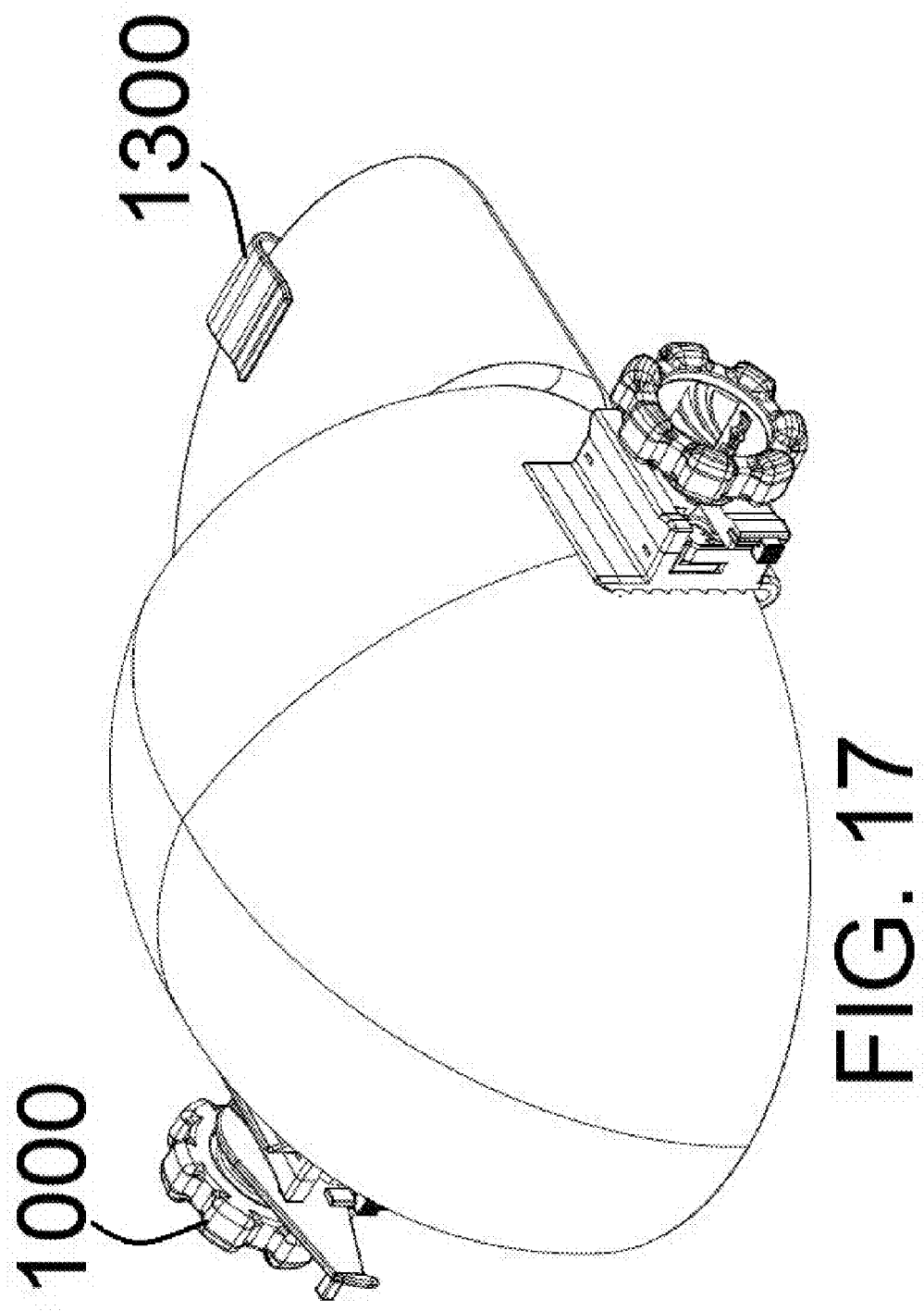
FIG. 17 is a diagram showing a perspective view of the baseball cap embodiment of FIG. 16.

FIG. 13 shows one embodiment of a brim clip 1300, FIG. 14 shows one embodiment of a gel pad 1400 with the brim clip, FIG. 15 shows one embodiment of a stabilizer 1500, and FIGS. 16 and 17 show the adapter system (FIG. 10), the brim clip (FIG. 13), the gel pad (FIG. 14), and the stabilizer (FIG. 15) installed onto a baseball cap. As shown in FIGS. 13 and 16A, the brim clip is a U-shaped clip that attaches to the brim of a baseball cap by a fabric band (preferably an elastic band). The gel pad (FIG. 14) attaches to the inside of the baseball cap near the brim, and is secured to the brim clip (FIG. 13) by the fabric (elastic) band. In some embodiments, the gel pad (FIG. 14) is also secured to the inside of the baseball cap with fasteners, such as Velcro® fasteners. The stabilizer (FIG. 15) extends from the adapter systems (FIG. 10) on each side of the baseball cap and connect together behind the gel pad (FIG. 14).

FIG. 15 shows one embodiment of a stabilizer having a strap 1510 and a snap 1520. In particular, FIG. 15A shows a top view of the stabilizer, FIG. 15B shows a side view of the stabilizer, and FIG. 15C shows a front view (FIG. 15C) of the stabilizer, while FIGS. 15D, 15E, and 15F show a side view, front view, and a top view of the snap 1520 that secures the strap 1510 to the adapter system (FIG. 10). The snap 1520 provides a mechanism by which the strap 1510 can be easily secured to the adapter system (FIG. 10). By providing a strap 1510 that partially circumscribes the baseball cap near the brim, the stabilizer (FIG. 15) provides greater stability for heavier safety gear, such as, for example, larger welding helmets, etc. Furthermore, interposing the gel pad (FIG. 14) between the stabilizer strap 1510 and the user provides greater comfort to the user.

Although FIG. 15 shows a snap 1520 to secure the strap 1510 to the adapter system (FIG. 10), it should be appreciated that, for other embodiments, a strap can be secured to the adapter system (FIG. 10) using different mechanisms. Various different embodiments of the stabilizer are shown with reference to FIGS. 18 through 22. It should be appreciated that these additional embodiments function in a manner similar to the embodiment of FIG. 15 to provide greater stability for welding helmets or other safety gear that is mounted to the adapter system (FIG. 10).

FIGS. 18A through 18F (collectively, FIG. 18) are diagrams showing another embodiment of a stabilizer. Specifically, FIG. 18A shows a left-side stabilizer strap 1810*a* that secures to a right-side stabilizer strap 1810*b*. The length of the stabilizer can be adjusted by securing the straps together at different lengths, similar to how one changes the length of a belt with reference to a belt buckle. The left-side stabilizer strap 1810*a* is secured to the adapter system (FIG. 10) on the left side of the baseball cap by using a left hinge 1820*a*, while the right-side stabilizer strap 1810*b* is secured to the adapter system (FIG. 10) on the right side of the baseball cap by using a right hinge 1820*b*. The stabilizer, in combination with the brim clip (FIG. 13), the gel pad (FIG. 14), and the adapter system (FIG. 10) provides a more secure mounting mechanism for heavier safety gear.

In yet another embodiment, as shown in FIGS. 19A through 19I (collectively, FIG. 19), the stabilizer can be secured to the adapter system (FIG. 10) using a detachable sliding mount, such as that shown in FIGS. 19D through 19I. In particular, a modified inner clip (FIGS. 19F, 19G, and 19H) secures to the baseball cap, and an insert (FIGS. 19C, 19D, and 19E) engages with the modified inner clip by sliding into a groove in the modified inner clip. Since one having ordinary skill in the art can discern the engagement mechanism from FIGS. 19A through 19I, further discussion of that engagement mechanism is omitted with reference to FIG. 19.

Figure 20A:
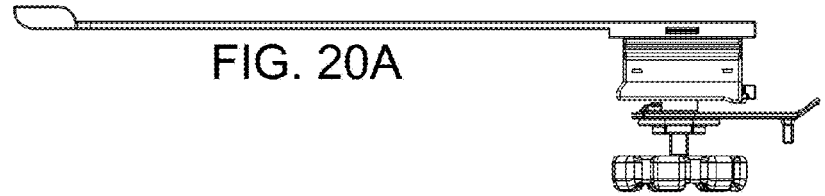
FIGS. 20A, 20B, 20C, 20D, 20E, 20F, and 20G (collectively abbreviated herein as "FIG. 20") are diagrams showing yet another embodiment of a stabilizer.
Figure 20B:
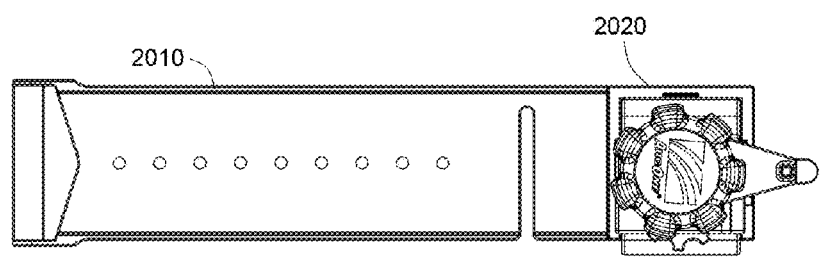
Figure 20E:
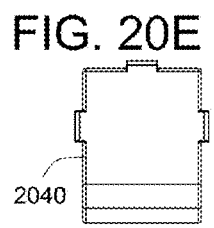
Figure 20F:
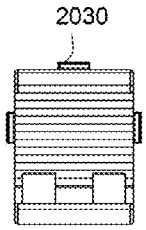
Figure 20D:
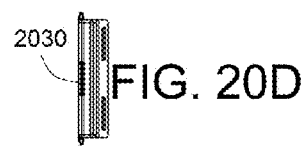
Figure 20G:
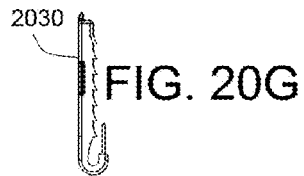
Figure 20C:
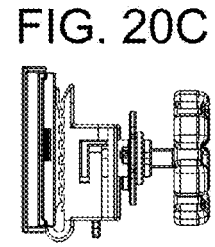

Also possible is the use of a three-snap mechanism 2020, as shown in the embodiment of FIGS. 20A through 20G (collectively, FIG. 20). Specifically, FIGS. 20D, 20F, and 20G show another modified inner clip 2030, which secures to a strap-clip 2040. Since the operation of the three-snap mechanism 2020 can be discerned with reference to FIGS. 20D through 20G by one having skill in the art, further discussion of the three-snap mechanisms 2020 is omitted with reference to FIG. 20.

FIGS. 21A through 21F (collectively, FIG. 21) are diagrams showing yet another embodiment of a stabilizer in which a side orifice is used to secure a stabilizer strap 2110 to the adapter system (FIG. 10). As shown in FIG. 21, the stabilizer strap 2110 comprises a set of flexible tabs 2120 that thread through a corresponding orifice in a modified clip 2130. The stabilizer strap 2110 can be released from the adapter system (FIG. 10) by squeezing together the flexible tabs 2120. Similar to FIG. 21, FIGS. 22A through 22F (collectively, FIG. 22) show a stabilizer that threads through the entire clip (rather than threading through an orifice on one side of the clip). Since the engagement mechanisms of FIGS. 21 and 22 can be discerned with reference to the drawings by those having skill in the art, further discussions of the engagement mechanisms in FIGS. 21 and 22 are omitted here.

As shown in FIGS. 13 through 22, by providing a stabilizing mechanism, heavier safety gear can be more-securely mounted to the baseball cap, thereby increasing safety and providing greater comfort to the user or operator.

Although exemplary embodiments have been shown and described, it will be clear to those of ordinary skill in the art that a number of changes, modifications, or alterations to the disclosure as described may be made. For example, while various embodiments are described with reference to safety equipment and protective head gear in work environments, it should be appreciated that the adapter can be used in different environments, such as, for example, athletic or sports environments. Additionally, for some embodiments, it should be appreciated that the adapter with the angle adjuster can be placed on both the left side and the right side of the head, thereby making the eventually-assembled headgear substantially symmetric about the sagittal plane of the head. In other alternative embodiments, the angle adjuster can be placed on only one side (i.e., either left side or right side) with the bearing on the other side. Also, it should be appreciated that the left side and the right side are interchangeable, since left and right are dependent on the perspective (e.g., whether facing toward the operator, or facing away from the operator). All such changes, modifications, and alterations should therefore be seen as within the scope of the disclosure.

What is claimed is:

1. An adapter system, comprising:
   a mount;
   a rear strap to mechanically couple to a rear of the mount;
   height-adjusting means for adjusting height, the height-adjusting means being pivotally coupled to the mount;
   an outer panel securely mounted to the mount;
   an unthreaded bore located in the outer panel;
   a cover to mate mechanically with the outer panel;
   a groove located in the cover;
   a rack located between the outer panel and the cover, the rack being slidably coupled with the mount to permit the rack to slide within the groove;
   teeth located on the rack; and
   a pinioned dial located between the outer panel and the cover, the pinioned dial comprising an axle mated with the unthreaded bore to permit rotational movement of the pinioned dial with reference to the outer panel, the pinioned dial engaging with the teeth on the rack, the engagement of the pinioned dial with the teeth on the rack forming a rack-and-pinion mechanism.

2. The adapter system of claim 1, further comprising an angle adjuster rotationally coupled with the rack to permit rotational movement of the angle adjuster with reference to the outer panel, the rotational movement of the angle adjuster being independent of rotational movement of the pinioned dial.

3. The adapter system of claim 1, further comprising a top fabric attachment means for attaching a top fabric, the top fabric attachment means being mechanically coupled to a top of the mount.

4. The adapter system of claim 1, further comprising a front fabric attachment means, the front fabric attachment means being mechanically coupled to a front of the mount.

5. The adapter system of claim 1, the rear strap being adjustable.

* * * * *